(12) United States Patent
Dunn

(10) Patent No.: US 9,078,435 B2
(45) Date of Patent: Jul. 14, 2015

(54) METHODS FOR DISINFECTING OR STERILIZING ARTICLES

(75) Inventor: Joseph Dunn, Lockport, IL (US)

(73) Assignees: Joseph Dunn, Daytona Beach, FL (US), part interest; PERFORMANCE PACKAGING OF NEVADA, LLC, Las Vegas, NV (US), part interest (*) Notice: Subject to any disclaimer, the term of this patent is extended or adjusted under 35 U.S.C. 154(b) by 621 days.

(21) Appl. No.: 13/228,105

(22) Filed: Sep. 8, 2011

(65) Prior Publication Data

US 2013/0065958 A1 Mar. 14, 2013

(51) Int. Cl.
| | |
|---|---|
| A01N 37/16 | (2006.01) |
| A01N 59/00 | (2006.01) |
| A61L 2/18 | (2006.01) |
| B65B 55/10 | (2006.01) |

(52) U.S. Cl.
CPC .............. *A01N 37/16* (2013.01); *A01N 59/00* (2013.01); *A61L 2/186* (2013.01); *B65B 55/10* (2013.01); *A61L 2202/23* (2013.01)

(58) Field of Classification Search
CPC .............. A61L 2/00; A61L 2/16; A61L 2/18; A61L 2/20; A61L 2/202; A61L 2/208; A61L 2202/00; A61L 2202/10; A61L 2202/11; A61L 2202/13
USPC ....................................................... 422/28–29
See application file for complete search history.

(56) References Cited

U.S. PATENT DOCUMENTS 5,620,656 A * 4/1997 Wensky et al. .................. 422/28

FOREIGN PATENT DOCUMENTS

EP 972758 A2 * 1/2000 ............ C07C 37/055

* cited by examiner

*Primary Examiner* — Sean E Conley
(74) *Attorney, Agent, or Firm* — Barnes & Thornburg LLP

(57) ABSTRACT

Disclosed herein are materials and methods for reducing, preventing, or eliminating the biological contamination of surfaces in spaces that are reasonably partitioned, defined or contained. A reagent that includes peroxides or molecules that includes peroxide bonds are contacted with at least one surface of an article. Some of these methods include disinfection within an apparatus and may include the step of volatilizing the peroxide bond containing agent, through, for example, vapor pressure and vaporization or evaporation effects, the addition of volatilization aids, or passive or assisted diffusion at modest temperatures and relatively long exposure times measured in some embodiments on the order of hours, days, or months. In some embodiments a liquid that includes a peroxide moiety is added (for example, during manufacture or subsequently) to a package, container, or any other reasonably partitioned or contained volume and allowed to migrate within the confined space for a period of time sufficient to disinfect the inner surfaces of the container and articles it contains.

18 Claims, 1 Drawing Sheet

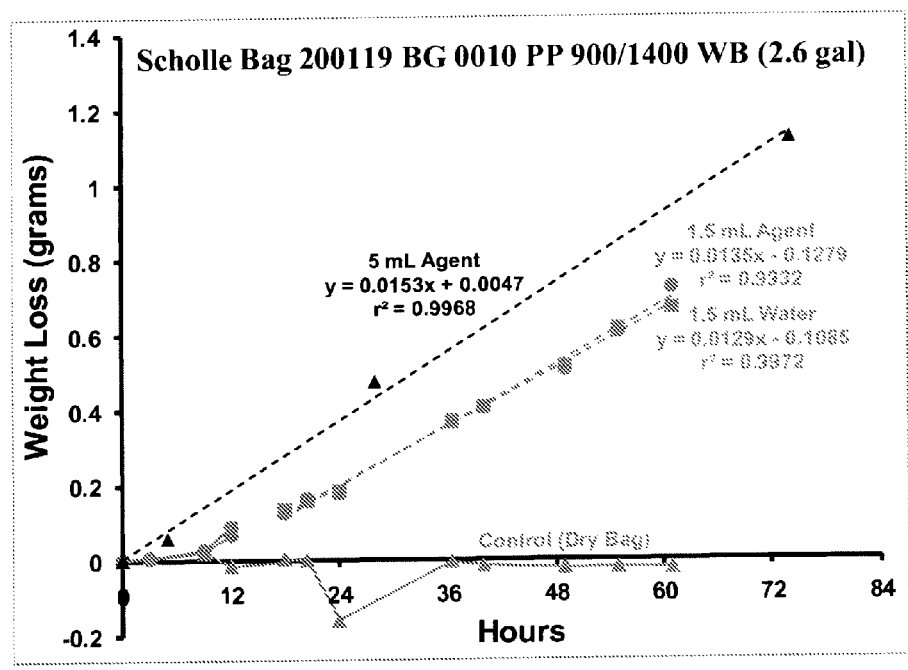

METHODS FOR DISINFECTING OR STERILIZING ARTICLES

FIELD OF THE INVENTION

This invention relates generally to materials and methods for sterilizing or disinfecting a variety of devices, articles and materials; these methods can be practiced in situ and include methods for eliminating or reducing the biological contamination of the interior volume and surfaces of containers or structures.

BACKGROUND

Microorganisms, such as bacteria, fungi and the like are virtually ubiquitous in the biosphere and while most are harmless, many have the capacity to infect humans, plants and animals while still others can cause spoilage of valuable foodstuffs and other materials. Accordingly, there exists a pressing, ongoing need to control, if not eliminate, unwanted microorganisms from a wide variety of surfaces. One of the most common methods of disinfecting or sterilizing surfaces is the use of heat, especially wet heat in the form of high pressure steam. Unfortunately, these methods do not work well with materials that are heat and/or water labile and oftentimes it is difficult if not impossible to employ these methods in situ.

For heat and/or moisture sensitive materials, alternatives to dry heat and/or steam must be used to control the biological contamination of these materials. Some of these alternatives include, but are not limited to, irradiation, exposure to toxic gases (for example, ethylene oxide, chlorine dioxide, or ozone), ultraviolet radiation, or treatment with chemical bactericides, fungicides and the like. Many of these methods are difficult to use with various articles of manufacture so there remains a need for new materials and methods for controlling microbial contamination on surfaces and articles. Some aspects of the instant invention address these needs.

SUMMARY

Some embodiments of the invention provide methods for disinfecting and/or sterilizing the interior volume and surfaces of sealed containers or structures using peroxides and molecules that include peroxide bonds. Some embodiments provide methods for disinfecting and/or sterilizing surfaces which leave behind small, generally recognized as safe (GRAS) levels of chemical residuals.

Some embodiments are methods performed using articles such as packages, containers, bags, pouches, packaging, wrappings, tubs, tins, bottles, buckets, and formed structures, or any other article; preferably those articles having a reasonably partitioned or defined space or volume within which a reagent that may include a peroxide is inoculated, sprayed, or otherwise placed in contact with at least one surface of the article. Some of these methods include disinfection within an apparatus and may include the step of volatilization of the peroxide bond containing agent, through, for example, vapor pressure and evaporative effects, the use of volatilization aids, or passive or assisted diffusion at modest temperatures and providing relatively long exposure times, measured in some embodiments on the order of hours, days, or months. In some embodiments a liquid that includes a peroxide moiety is added (for example, during manufacture or subsequently) to a package, container, or any other reasonably partitioned volume and allowed to migrate within the defined space for a period of time sufficient to disinfect the inner surfaces of the container.

Some embodiments of the present invention also use as the active agent performic acid (generated by the mixture of water, formic acid, and hydrogen peroxide with or without volatilization aids) for the control or elimination of microorganisms from surfaces.

Some embodiments include methods for controlling contamination within a partitioned or otherwise defined space, comprising the steps of contacting surfaces within a partitioned or otherwise defined space with a chemical in the vapor phase. In some embodiments the chemical in the vapor phase is selected from the group consisting of: peroxides, peracids, or moieties that include at least one peroxide bond. In some embodiments the surfaces are exposed to the chemical in its vapor phase for at least 5 minutes at a temperature below 50 C. In some embodiments the partitioned or otherwise defined space includes at least one article that is not an integral part of the partitioned or defined space or volume.

In some embodiments the partitioned of otherwise defined space is a container. In some embodiments the container is selected from group consisting of: packaging, containers, bags, pouches, cans, tins, buckets, tubs, bottles, ampoules, barrels, sleeves, capsules, boxes, other formed packages or structures, and the like. In some embodiments the containers are flexible. And in other embodiments the containers are rigid. In some embodiments the container may include at least one accessory or feature. In some embodiments the accessory or feature is selected from the group consisting of: fitments, valves, bungs, lids, vents, ports, spouts, drains, covers and caps, seals, or membrane seals.

In some embodiments surfaces of or within a partitioned or defined space or volume are incubated with a peroxide, peracid, or a mixture of compounds, one or more of which includes a peroxide bond for longer than about five minutes. In some embodiments the temperature the incubation step occurs at a temperature equal to or less than about 50 C. In some embodiments a peroxide concentration equal to or greater than about 2% is added to or used in a partitioned or defined space to form a peracid or a mixture of compounds one or more of which includes a peroxide bond.

In some embodiments the peroxide mixture added to or used in the partitioned or defined space includes formic acid (methanoic acid) or performic acid (permethanoic acid) either of which may be added to or present at a concentration greater than or equal to about 2%. In some embodiments the peroxide mixture added to or used in the partitioned or defined space includes peracetic acid (ethanoic acid) or peracetic acid (perethanoic acid), or propionoic acid (propanoic acid) or propionoic peracid (propanoic peracid), or a mixture of these with or without the addition of formic acid, any of or the combination of which is added or present at a concentration greater than or equal to 2%. In some embodiments the peroxide mixture added to or used in the partitioned or defined space includes at the time of addition, or subsequently evolves to form, a mixture that is generally recognized as safe for consumption or other usage.

Still other embodiments include methods for reducing the number of biological contaminants in a partitioned or otherwise defined space or volume, comprising the steps of: mixing formic acid, hydrogen peroxide and water with or without the addition of other compounds; wherein the mixture produces performic acid in situ; and contacting at least one surface with said performic acid formed in situ wherein the surface is within a partitioned or otherwise defined space or volume. In some of these embodiments the space or volume is the interior of a container. In some embodiments the container is selected from the group consisting of; packaging, bags, pouches, cans, tins, boxes, buckets, tubs, bottles, ampoules, barrels, sleeves, formed packages or structures or the like. In some embodiments the partitioned or otherwise defined space or volume includes at least one article and the article is present in the space or volume at the same time as a microbiocidal concentration of peracid or peroxide bond containing vapors. In some embodiments the interior of the container includes at least one article inside the container at the same time as a microbiocidal concentration of peracid or peroxide bond containing vapors.

Still other embodiments include systems for controlling contamination within a partitioned or otherwise defined space or volume comprising: a vapor that includes a microbiocidal concentration of peracid or peroxide bonds within a partitioned or otherwise defined space or volume, wherein the concentration of vapors is such that at least about 5 minutes of contact between the vapor and an interior surface of the space or volume is sufficient to inactivate at least about 90 percent of the microbes within the space or volume. In some embodiments the vapor is formed by a mixture that includes peracid or peroxide formic acid (methanoic acid) or performic acid (permethanoic acid) either of which is added or present at a concentration greater than or equal to about 2%. In some embodiments the system is used to treat the interior of a container which may or may not house an article that is not an integral part of the container.

BRIEF DESCRIPTION OF THE FIGURES

FIG. 1. Graph of the change in weight over time of polyolefin bags containing water or a disinfecting mixture. The weight loss is due to migration of water and/or components of the disinfection mixture through the walls of the bag.

DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended; such alterations, modifications, and further applications of the principles of the novel technology being contemplated as would normally occur to one skilled in the art to which the novel technology relates are within the scope of this disclosure and what it claims.

Unless specifically stated or clearly implied the term 'about' as used herein refers to a range of values from less than to greater than 10 percent of the stated value. For example, about 1 refers to the range of values from 0.9 to 1.1

Multiple methods and features of the present invention are novel in relation to current practice. Though peroxide and peracids are commonly used for disinfection and sterilization of containers and packaging(s), they are most often employed so as to produce rapid activity for on-line disinfection at relatively short exposure times. The active agents are generally applied by immersion, spraying, filling, or other methods designed to distribute the active agents rapidly and throughout or over the product to be disinfected or sterilized. The disinfection agents are most often used at high concentration and volume, and/or with the addition of a stimulant such as heat, ultraviolet light, a plasma rich environment, or the like in order to activate the oxidative activity of the peroxide-moiety and accelerate its decay and attendant release of its oxidative capacity.

Contrary to currently used commercial methods the present invention uses relatively small volumes of disinfecting reagents, and relatively long times of exposure (for example, hours or days) to produce disinfection or sterilization while yielding low levels of residual compounds. The active agents employed in the present invention are distributed throughout the treated product by evaporation and other volatilization means followed by passive or facilitated diffusion.

Some embodiments of the instant invention generate performic acid in situ. In some embodiments performic acid mixtures are produced by combining water, formic acid, and hydrogen peroxide inside of the space that is to be disinfected. The utility of this approach may be further extended by partitioning or confining the space so as to allow the concentration of performic acid or vapors from performic acid to accumulate in the given space. Given enough time and the necessary amount of performic acid in a given substantially confined or otherwise partitioned space, this reagent can be used for the in situ sterilization of surfaces in a partitioned space or volume.

Peroxide or peracid based reagents used for disinfecting or sterilizing surfaces are usually used in combination with accelerators of peroxide decomposition such as heat, ultraviolet light, plasmas, or other activators which speed-up the formation of hydroxyl radicals. In contrast, many of the embodiments of the present invention can be practiced without the need for such accelerants of peroxide decomposition. These methods are especially useful for the disinfection and/or or sterilization of sealed containers, such as packages, containers, bags, pouches, tanks; tubs, bottles, buckets, sleeves or other formed structures, using a small volume of hydrogen peroxide or another peracid agent, in conjunction with long contact time. The peroxide bond rich vapor migrates within the container and produces microbial disinfection on the surfaces and the volume within the container through oxidative effects acting over a relatively long time of exposure (for example, hours or days rather than a few seconds or minutes) at ambient or modestly elevated temperatures.

Some embodiments of the current invention are especially well suited for the sterilization of bags for use in bag-in-box (BIB) applications within the food and beverage industry. Currently, bags for BIB applications are manufactured at one site and then the bag/fitment combination is sterilized at a second site using irradiation. Sterilization by irradiation in this process usually requires that the bags be transported to a distant irradiation facility, inserted into the irradiation processing queue, and transported back to the originator for sale and distribution following irradiation sterilization. This process is expensive due to the required shipping and processing (the irradiation process itself is relatively expensive in part because of the high capital costs associated with the facility and shielding of the radiation source), and time consuming (typically, the minimum time required for the round trip is one to two weeks or more).

In contrast, invention methods discussed herein can be used virtually anywhere. In some embodiments of the invention a small volume of a reagent that may include a peroxide or peracid mixture is employed. The reagent may be sprayed, painted, or otherwise dispensed into a bag, or a portion of the bag, or the neck of a fitment that opens into the bag before, or during, the attachment of the fitment to the bag. Volatilization of the active compounds within the bag disinfects the inner volume and surfaces of the bag including surfaces of the bag that are not in direct contact with the liquid or solid form of the peroxide containing reagent. In some embodiments, the active disinfection mixture may be added to a fitment containing a membrane seal, and/or to a bag to which the fitment is subsequently affixed. By controlling the volume of disinfectant employed and/or continued disintegration of the active chemistries, it is usually possible to generate harmless and generally recognized as safe residuals and residual levels in the bag at the time of filling. Accordingly, aspects of the present invention provide relatively rapid and inexpensive methods (relative to the transportation and processing times and costs generally attendant to conventional radiation processing) for disinfecting or sterilizing surfaces in confined spaces such as bags. These methods are readily adaptable for BIB applications.

In still other embodiments these methods are used to sterilize or disinfect medical products or devices packaged for use at a later time, examples of such products, include, but are not limited to scalpels or scalpel blades, luers, shunts, catheters, sutures, and implants packaged in a wrap or container eventually sealed to exclude re-contamination by microorganisms. The inclusion of a small volume of disinfectant (according to some embodiments of the present invention) before sealing of the package provides a reagent for disinfecting or sterilizing the interior of the package and the surfaces of any article(s) within the package. These inventive methods enable the manufacturer to avoid costly radiation or other energy intensive methods of sterilization or disinfection, such as use of a retort.

EXPERIMENTS AND EXEMPLARY RESULTS

Experiment 1

About two or three droplets of 3% hydrogen peroxide were dropped into a 4 ounce PET bottle before capping; the peroxide was omitted from two bottles which were used as control samples. Before sealing, the inside surface of the bottle cap (liner removed) or its foam liner had been inoculated with a 10 μL droplet of *Bacillus atrophaeus* ATCC 9372 spores dried down onto the cap or liner surface. *Bacillus atrophaeus* ATCC 9372 spores are known to be of relatively high resistance to peroxide disinfection and are a recommended (for example, the U.S. Pharmacopeia) resistant organism for disinfection studies using chemicals (such as peroxide or ethylene oxide) or dry heat.

After standing overnight (15 hours) at 35 C the bottles were opened and the inoculated areas (of both untreated, control bottles and bottles to which hydrogen peroxide had been added) were swabbed to sample the level of recoverable viable spores. The results obtained are shown in Table 1 below. The level of spores recoverable from bottles to which 3 drops of 3% hydrogen peroxide had been added was less (reductions >90% or >1 logarithm lower) than that from control bottles to which no hydrogen peroxide had been added. Thus, the hydrogen peroxide mixture used in this experiment did reduce the level of recoverable viable spores and show some disinfection capability, however, the level of efficacy was small and insufficient to prove useful for the purposes of sterilization.

TABLE 1

The recovery of *Bacillus atrophaeus* spores from 4 oz. PET bottles incubated with (3 Drops, Overnight) or without (None, Recovery Control) the addition of 3% hydrogen peroxide.

| Site of Inoculation | Treatment | CFU Recovered | Log Recovery | Log Reduction |
|---|---|---|---|---|
| Liner | None (Recovery Control) | 2300000 | 6.4 | NA |
| Cap | None (Recovery Control) | 6600000 | 6.8 | NA |
| Liner | 3 Drops, Overnight | 830000 | 6 | 0.4 |
| Cap | 3 Drops, Overnight | 425000 | 5.6 | 1.2 |
| Cap | 3 Drops, Overnight | 475000 | 5.7 | 1.1 |

Experiment 2

A 10 microliter droplet of water containing *Bacillus atrophaeus* spores was dried onto the inner surface of the fitment from a Scholle Clean-Clic® 4L (BG 0004 PM 900/8CC21 WB) bag-in-box bag. One milliliter of a performic acid mixture produced by a combination of water, formic acid, and hydrogen peroxide was placed in the bottom of the bag and the fitment then reinstalled; replicate inoculated fitments were placed on bags without the addition of performic solution in order to serve as control samples. The bags were stored at ambient conditions (approximately 65-75° F.) for one week, the inoculation site on each fitment was then swabbed, the swabs shaken in 3 mL of a saline solution to harvest the recovered spores, and the harvest medium or its serial ten-fold dilutions spread plated on tryptic soy agar medium and incubated for 48 hours at 35 C. The number of viable *Bacillus atrophaeus* spores recovered from untreated (Recovery Control) or performic treated bags is shown in Table 2.

TABLE 2

The number of colony forming units (CFU) recovered from fitments of bags incubated without (Recovery Control) or with the addition of a performic mixture.

| Sample | CFU Recovered | Log CFU Recovered | Log Reduction |
|---|---|---|---|
| Recovery Control | 63800 | 4.8 | NA |
| Recovery Control | 4300 | 4.6 | NA |
| Treated | 0 | <0 | >4.7 |
| Treated | 0 | <0 | >4.7 |

As illustrated by the data summarized in Table 2, no viable spores were recovered from the performic treated bag sample fitments, while 46,000 CFU or more of spores were recovered from the fitments on untreated, control bags.

Experiment 3

As in Experiment 2, a 10 microliter droplet of water containing *Bacillus atrophaeus* spores was dried on the inner surface of the fitment from a Scholle Clean-Clic® 4L (BG 0004 PM 900/8CC21 WB) bag-in-box bag. The inoculum level used was significantly greater than was used in Experiment 2. The inner surface of a fitment cap was provided with a 10 microliter water droplet containing greater than 10,000,000 (10 million) colony forming units of *Bacillus atrophaeus* spores and was dried. The spore inoculation site on each fitment was clearly visible after drying and it was evident that the spot contains a very high concentration of spores. The area of the spot is about 0.4 cm2 and it contains greater than 10,000,000 spores (a spore concentration greater than 25 million spores per square centimeter). This is a relatively high level of inoculation and the spore mass at the inoculation site is clearly visible. The 10 microliter water droplet dried onto the fitment and a thick outer ring of spores formed as the droplet dried; a portion of this thick outer ring dislodged from the upper part of the dried droplet during handling of the fitment. This outer ring contains a thick biomass of spores deposited one on top of the other many spores deep.

About one milliliter of a performic acid mixture produced by a combination of water, formic acid, and hydrogen peroxide was placed in the bottom of the bag and the fitment then reinstalled; replicate inoculated fitments were placed on bags without the addition of performic solution in order to serve as control samples. The bags were stored at ambient conditions (approximately 65-75° F.) for 20, 44, and 68 hours and the inoculation site on each fitment was then swabbed, recovered, and counted as in Experiment 2. The number of viable *Bacillus atrophaeus* spores recovered from untreated (Recovery Control) or performic treated bags is shown in Table 3 below. Some surviving spores were recovered from one of the treated samples after 20 hours of treatment (but not the replicate sample), but no viable spores were recovered on any of the treated samples thereafter. About 7.5 logarithm cycles of viable spores (or more than 10 million CFU) were recovered from the untreated, control samples.

TABLE 3

The number of colony forming units (CFU) recovered from fitments of bags incubated without (Recovery Control) or with the addition of 1 mL of a performic mixture. Treated samples were assayed after 20, 44, and 68 hours; the control samples were assayed at 20 and 68 hours.

| Sample | CFU Recovered | Log CFU Recovered | Log Reduction |
|---|---|---|---|
| Recovery Control | 34300000 | 7.5 | NA |
| Recovery Control | 31400000 | 7.5 | NA |
| 20 Hrs | 225 | 2.4 | 5.1 |
| 20 Hrs | 0 | <0 | >7.5 |
| 44 Hrs | 0 | <0 | >7.5 |
| 44 Hrs | 0 | <0 | >7.5 |
| 68 Hrs | 0 | <0 | >7.5 |
| 68 Hrs | 0 | <0 | >7.5 |

Experiment 4

As in Experiments 2 and 3, a 10 microliter droplet of water containing *Bacillus atrophaeus* spores was dried onto the inner surface of the fitment from a Scholle Clean-Clic® 4L (BG 0004 PM 900/8CC21 WB) bag-in-box bag. The inoculum level used was high as in Experiment 3. For treatment, 300 microliters or 100 microliters of a performic acid mixture produced by a combination of water, formic acid, and hydrogen peroxide was placed in the bottom of a bag and the fitment then reinstalled; a replicate inoculated fitment was placed on a bag without the addition of performic solution in order to serve as a control sample. The bags were stored at ambient conditions (approximately 65-75° F.) for 50 hours and the inoculation site on each fitment was then swabbed, recovered, and counted as in Experiments 2 and 3. The number of viable *Bacillus atrophaeus* spores recovered from untreated (Recovery Control) or performic treated bags is shown in Table 4 below. No surviving spores were recovered from either of the treated samples. About 7.7 logarithm cycles of viable spores (or more than 10 million CFU) were recovered from the untreated, control sample.

After the 50 hour incubation at ambient conditions, sample bags treated with 100 microliters of the performic solution were filled with 3 liters of water, shaken, and then sampled and assayed for peroxide residuals using CHEMetrics, Inc. (4295 Catlett Rd., Calverton, Va. 20138) Chemets K-5510 assay procedures. The peroxide residuals were 1 part per million (ppm, mg/L) in the water sample. A peroxide residuals reading was also taken on a bag treated with 100 microliters of the performic solution and assayed after 9 days of incubation at ambient conditions. Again the bag was filled with 3 liters of water, shaken, and then sampled and assayed as before. The peroxide residuals were now between 0.6 and 0.8 ppm in the water sample.

TABLE 4

The number of colony forming units (CFU) recovered from fitments of bags incubated without (Recovery Control) or with the addition of either 300 microliters or 100 microliters of a performic mixture. Samples were assayed after 50 hours at room temperature.

| Sample | CFU Recovered | Log CFU Recovered | Log Reduction |
|---|---|---|---|
| Recovery Control | 54100000 | 7.7 | NA |
| 300 microL, 50 Hrs | 0 | <0 | >7.7 |
| 100 microL, 50 Hrs | 0 | <0 | >7.7 |

Experiment 5

As in Experiments 2, 3, and 4, a 10 microliter droplet of water containing *Bacillus atrophaeus* spores was dried on the inner surface of the fitment from a Scholle Clean-Clic® 4L (BG 0004 PM 900/8CC21 WB) bag-in-box bag. The inoculum level used was a one-to-ten dilution of that used in Experiments 3 and 4. For treatment, 25 microliters of a performic acid mixture produced by a combination of water, formic acid, and hydrogen peroxide was placed in the bottom of a bag and the fitment then reinstalled; a replicate inoculated fitment was placed on a bag without the addition of performic solution in order to serve as a control sample. The bags were stored at ambient conditions (approximately 65-75° F.) for 46 and 122 hours and the inoculation site on each fitment was then swabbed, recovered, and counted as previously described. The number of viable *Bacillus atrophaeus* spores recovered from untreated (Recovery Control) or performic treated bags is shown in Table 5 below. Surviving spore recovery from either of the treated samples was significantly less than that from the untreated, control samples.

After the 33 hours at ambient conditions incubation, a sample bag treated with 25 microliters of the performic solution was filled with 3 liters of water, shaken, and then sampled and assayed for peroxide residuals using the Chemets K-5510 assay procedures. The oxidative peroxide residuals were 0.3 parts per million (ppm) in the water sample. A second oxidative peroxide residuals reading was taken after 122 hours of incubation at ambient conditions. Again the bag was filled with 3 liters of water, shaken, and then sampled and assayed as before. The oxidative peroxide residuals level was now 0.2 ppm in the water sample. The regulatory limit for oxidative peroxide residual levels under these conditions is 0.5 ppm; clearly the disinfection process yielded peroxide oxidative levels well below the regulatory limit.

TABLE 5

The spore recovery from fitments of bags incubated without (Recovery Control) or with the addition of either 25 microliters of a performic mixture. Samples were assayed after 46 and 122 hours at room temperature.

| Sample | CFU Recovered | Log CFU Recovered | Log Reduction |
|---|---|---|---|
| Recovery Control | 2,600,000 | 6.4 | NA |
| Recovery Control | 2,650,000 | 6.4 | NA |
| 25 microL, 46 Hrs | 2280 | 3.4 | 3.0 |
| 25 microL, 122 Hrs | 8 | 0.9 | 5.5 |

Experiment 6

The effect of concentration of the added disinfection mixture was investigated by comparing 500 microliter of the disinfection mixture used in the previous demonstrations (call this mixture a 1× concentration of the disinfecting agent) and 200 microliters of a mixture containing 3.8 times the level of peroxide as the 1× concentration mixture.

As in many of the previous exhibits, a 10 microliter droplet of water containing *Bacillus atrophaeus* spores was dried on the inner surface of the fitment from a Scholle Clean-Clic® 4L (BG 0004 PM 900/8CC21 WB) bag-in-box bag. For treatment, each of the two volumes and concentration mixture combinations of water, formic acid, and hydrogen peroxide were placed in the bottom of a bag and the fitment then reinstalled; a replicate inoculated fitment was placed on a bag without the addition of performic solution in order to serve as a control sample.

The results obtained from this experiment are summarized in Table 6. These data illustrate that by elevating the concentration of the disinfection mixture added to the package it is possible to accelerate the migration/permeation of the disinfection mixture within the bag.

TABLE 6

The effect of the concentration of the disinfection mixture on the time required to produce disinfection and sterilization within a treated bag.

| | |
|---|---|
| Untreated, Control | 7.3 Logarithm Cycles of Colony Forming Units Recovered |
| 1X Concentration 500 µL for 17 Hours | 6.6 Logarithm Cycles of Colony Forming Units Recovered |
| 3.8X Concentration 200 µL for 17 Hours | 3 Colony Forming Units Recovered |

Experiment 7

Demonstration tests were performed to document the ability of this method to effectively disinfect and sterilize even larger packages than the 4 liter bags employed previously. Fifty seven and nine-tenths (57.9) gallon bags were used for these tests (Scholle 200301 BG 0220 APHM 800/800X). For these tests, a 10 microliter droplet of water containing *Bacillus atrophaeus* spores was dried on the inner surface of the fitment and also onto the inner surface of the bag immediately beneath the fitment.

Five milliliters or 2.5 mL of the disinfection mixture (1× concentration) was placed in the bag as low and as far below the fitment as possible and the bag held upright and shaken slightly in order to cause the disinfection mixture to run to the bottom of the bag. One bag to which 5 mL of disinfection mixture was added and one bag to which 2.5 mL was added were incubated at ambient temperatures in an unfolded flat position, and one bag to which 5 mL of disinfection mixture was added was folded before incubation (see FIG. 3).

The bags were incubated for thirteen days and the results obtained for the number of viable *Bacillus atrophaeus* spores recovered from an untreated (Control) bag or the bags to which the disinfection mixture had been added are summarized in Table 7 below.

TABLE 7

The numbers of viable colony forming units recovered from 57.9 gallon drum bags.

| | Innoculation Site | |
|---|---|---|
| Sample | Fitment | Bag |
| Control | 6.73 Log CFU | 6.72 Log CFJ |
| 5 mL of 1X Concentration | 0 CFU | 0 CFU |
| 2.5 mL of 1X Concentration | 0 CFU | 0 CFU |
| Folded Bag | 0 CFU | 0 CFU |

As a test, and in order to demonstrate the ability of the disinfecting mixture to migrate past folds, two 57.9 gallon drum bags were incubated in a flat position or after careful folding (attempting to retain the added disinfection mixture in the bottom of the bag). After swab recovery of the *Bacillus atrophaeus* spores from the two inoculation sites on the disinfection mixture treated bags, the bags were filled with 57.5 gallons (483 pounds) of water, mixed, and then sampled and assayed for peroxide residuals using the Chemets K-5510 assay procedures. The oxidative peroxide residual determinations obtained are shown in Table 8.

TABLE 8

The oxidative residual levels obtained from 57.9 gallon drum bags after 13 days.

| | |
|---|---|
| 5 mL of 1X Concentration | 0.3 mg/L |
| 2.5 mL of 1X Concentration | 0.1 mg/L |
| Folded Bag (5 mL of 1X) | 0.4 mg/L |

Experiment 8

This exhibit is an extension of the methods and results shown in Experiment 7 using the same 57.9 gallon drum bags used in Experiment 7 (Scholle 200301 BG 0220 APHM 800/800X). The volumes and disinfection mixture concentrations employed are shown in Table 9. The tested volumes and concentrations of the disinfection mixture were able to inactivate all the inoculated *Bacillus atrophaeus* spores after incubation for about four (4) days at ambient conditions. Note that in these trials the disinfection mixture was deposited at the foot end of the bag opposite the fitment, the bag folded so as to retain the disinfection mixture at that end of the bag during the folding process, and the bag was then incubated in this folded position; the disinfection mixture was nevertheless able to still migrate across the folding pattern to inactivate spores inoculated on the fitment. Greater than 6 (6.4) logarithm cycles of viable spore colony forming units were recovered from the untreated, control bag. Referring now to Table 9. In both trials the disinfection mixture was deposited at the foot end of the bag opposite the fitment, the bag folded, and the bag treated in a folded position. Also, in these particular tests the oxidative potential of the residual contents of the bag after filling with 5.3 gallons of water were below the regulatory maximum (regulatory limit is 0.5 mg/L) as the level of recovered residuals in these tests were 0.1 and 0.2 mg/L. These results show that it is possible to sterilize these large bags (57.9 gallons) during room temperature storage in as short a time as four days and with negligible and generally recognized as safe levels of residuals.

TABLE 9

Recovery of viable spores and oxidative residuals from 57.9 gallon drum bags after about 4 days of ambient incubation.

| 95.5 Hrs | 4 mL | 0 CFU Recovered | Residuals | Log Red |
|---|---|---|---|---|
| Concentration | 4.5 X | 0 CFU Recovered | 0.1 mg/L | >6.4 |
| 95 Hrs | 6 mL | 0 CFU Recovered | Residuals | Log Red |
| 96 Hrs | Control | | 6.53 Log CFU Recovered | |
| 96 Hrs | Control | | 6.32 Log CFU Recovered | |

Experiment 9

The previous exhibits employed bags with relatively high barrier properties, i.e., the disinfectants and sterilants added were confined to the bag, the materials and construction of the bags being relatively inhibitory to the migration of moisture or gasses through the walls of the bag.

In this experiment, a polyolefin bag (Scholle 2.6 gallon 200119 BG 0010 PP 900/1400 WB) with significantly lower barrier properties (a bag relatively more permeable to moisture vapor or gasses) was employed to demonstrate the efficacy of the method even under such conditions and with such materials wherein the treated container is not strictly hermetic nor the treated volume strictly confined.

During initial trials, adding up to even 1 milliliter of the disinfection mixture at the 1× concentration yielded no significant *Bacillus atrophaeus* spore inactivation even after 55 hours of ambient incubation. Subsequent trials using 1.5 mL and 2.5 mL of the 1× concentration of the disinfection mixture yielded 2 logarithm cycles or less inactivation after 141 hours (>5.8 days) of ambient incubation using a 6 logarithm cycle inoculation level of *Bacillus atrophaeus* spores.

After these poor initial results, a weight loss study was performed. Referring now to FIG. 1. The graph in FIG. 1 illustrates the loss of weight when 1.5 mL of water, 1.5 mL of the disinfection mixture at the 1× concentration, or 5 mL of the 1× concentration disinfection mixture were sealed into the bag and incubated at ambient conditions inside a sealed chamber containing Drierite (W. A. Hammond Drierite, Ltd, Xenia, Ohio). An approximately 0.013 to 0.015 grams per hour loss in weight from the bag was observed. The results obtained clearly demonstrate that during incubation, compounds in the bag are migrating through the packaging material and being lost to the environment surrounding the bag.

The migration through the bag (effusion) necessitates an adjustment of the composition and amount of disinfection mixture needed to be added to the bag in order to achieve sterilization. Follow on experiments examined the effects of using different concentrations and volumes of the disinfection mixture. As in previous experiments, a 10 microliter droplet of water containing *Bacillus atrophaeus* spores was dried on the inner surface of the fitment from each of a duplicate series of bags. In each of the test bags, the volume of disinfection mixture at the concentration listed in Table 10 was deposited near the center of the bag, the fitment replaced on each bag, and the bag incubated for 23 or 25 hours at ambient temperatures (see Table 10), at which time the inoculation site on each fitment was swab recovered and viable spores enumerated.

The results summarized in Table 10 illustrate that in these 2.6 gallon polyolefin bags a range of disinfection mixture concentrations and added volumes were able to inactivate all or nearly all of the *Bacillus atrophaeus* spores within about a day of incubation at ambient temperatures and conditions. These results clearly demonstrate that an appropriate volume and concentration of the disinfection mixture can be used to disinfect and sterilize the internal volume of polyolefin bags.

TABLE 10

The disinfection and sterilization effects of using various volume and concentration combinations to treat 2.6 gallon polyolefin bags. (Log Red is a convenient abbreviation for Logarithm Cycle Reduction in Spore Viability).

| 25 Hrs | 200 μL | 0 CFU Recovered | Residuals | Log Red |
|---|---|---|---|---|
| Concentration | 2.7 X | | 0.15 mg/L | >7.31 |
| 23 Hrs | 200 μL | 0 CFU Recovered | Residuals | Log Red |
| Concentration | 4.5 X | | 0.3 mg/L | >7.31 |
| 25 Hrs | 150 μL | 6.64 Logs Recovered | Residuals | Log Red |
| Concentration | 1.3 X | | 0.05 mg/L | 0.66 |
| 23 Hrs | 150 μL | 0 CFU Recovered | Residuals | Log Red |
| Concentration | 2.2 X | | 0.0 mg/L | >7.31 |

Experiment 10

This exhibit is an extension of the methods and results shown in Experiment 9 to a second, larger a polyolefin bag (Scholle 200233 BG 0020 PP 900/1400). The volumes and disinfection mixture concentrations employed are shown in Table 11. Again it was seen that the selected volume and concentration of the disinfection mixture was able to inactivate all the inoculated *Bacillus atrophaeus* spores after one day or ambient incubation. Note that in one trial the disinfection mixture was deposited at the foot end of the bag opposite the fitment, the bag folded so as to retain the disinfection mixture at that end of the bag during the folding process, and then the bag incubated in this folded position; the disinfection mixture was nevertheless still able to migrate (across the folding pattern) to inactivate spores inoculated on the fitment. Greater than 7 (7.14) logarithm cycles of viable spore colony forming units were recovered from the untreated, control bag.

Referring now to Table 11. In these particular tests the oxidative potential of the residual contents of the bag after filling with 5.3 gallons of water were about twice the allowable regulatory maximum (regulatory limit is 0.5 mg/L; recovered residual levels in these tests were 1.0 mg/L).

TABLE 11

The disinfection and sterilization effects of using various volume and concentration combinations to treat 5.3 gallon polyolefin bags.

| 24 Hours | 400 mL | 0 CFU Recovered | Residuals | Log Red |
|---|---|---|---|---|
| Concentration | 4.5X | | 0.1 mg/L | .7.14 |
| 24 Hours Repeat | 400 mL | 0 CFU Recovered | Residuals | Log Red |
| Concentration | 4.5X | | 0.1 mg/L | >7.14 |
| 24 Hours Folded | 400 mL | 0 CFU Recovered | Residuals | Log Red |
| Concentration | 4.5X | Folded | 0.1 mg/L | >7.14 |

While the novel technology has been illustrated and described in detail in the figures and foregoing description, the same is to be considered as illustrative and not restrictive in character, it being understood that only the preferred embodiments have been shown and described, and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

I claim:

1. A method for controlling contamination within a package, container, or otherwise sealed, partitioned, or defined space, comprising:
   providing a container defining an enclosed space and having an article to be disinfected,
   placing a chemical comprising a mixture of water, hydrogen peroxide and formic acid inside the container with the article,
   sealing the container with the article inside the container,
   exposing surfaces within the container to evolved vapors or gases from the mixture for at least 1 hour at a temperature at or below 50° C. and without exposing the mixture to microwave radiation for forming a plasma,
   removing the disinfected article from the container.

2. The method according to claim 1, wherein the container is a flexible container.

3. The method according to claim 1, wherein the container is a rigid container.

4. The method according to claim 1, wherein the container further includes at least one accessory selected from the group consisting of: fitments, valves, bungs, lids, vents, ports, spouts, drains, covers and caps, seals, or membranes.

5. The method according to claim 1, wherein the mixture contains a hydrogen peroxide concentration equal to or greater than about 2%.

6. The method according to claim 1, wherein the mixture contains an acid concentration equal to or greater than about 2%.

7. The method according to claim 1, wherein the mixture contains addition supplements that increase or elevate the vapor pressure of the aqueous mixture.

8. The method according to claim 1, wherein the container is selected from the group consisting of: package, pouches, containers, bag, bag-in-box packages, ampoules, cans, tins, bottles, barrels, buckets, capsules, sleeves, or otherwise lidded or sealed formed packages or structures, or the like.

9. The method according to claim 1, wherein the concentration and oxidizing capacity of the mixture diminishes over time and the initial concentration or remaining residue from the mixture is too low to pose an unacceptable threat to human or animal health.

10. A method for controlling contamination within a package, container, or otherwise sealed, partitioned, or defined space, comprising:
    providing a package enclosing an article to be sanitized,
    placing water, formic acid and hydrogen peroxide inside the package,
    sealing the package, and
    generating performic acid inside the package without the application of heat, plasmas and other activators and sanitizing the article.

11. The method according to claim 10, wherein the generating comprises volatilizing the performic acid and exposing the inner surfaces of the package to the volatilized performic acid for at least two hours.

12. The method according to claim 10, wherein the volume of water, formic acid and hydrogen peroxide is less than 2.5 ml.

13. The method according to claim 10, comprising
    providing partitioned spaces in the package, and
    exposing the inner surfaces of the package and the partitioned spaces to the performic acid for at least two hours.

14. The method according to claim 13, wherein the placing step occurs in only one of the partitioned spaces.

15. The method according to claim 12, wherein the article is a scalpel.

16. The method according to claim 10, wherein the volume of water, formic acid and hydrogen peroxide greater than 2.5 ml.

17. A method for controlling contamination within a package, container, or otherwise sealed, partitioned, or defined space, comprising:
    providing a package,
    placing a mixture of about 2.5 ml of water, formic acid and hydrogen peroxide inside the package,
    sealing the package, and
    generating performic acid inside the package without the application of heat, plasmas and other activators.

18. A method for controlling contamination within a package, container, or otherwise sealed, partitioned, or defined space, comprising:
    providing a package,
    placing an article in the package,
    placing a mixture of not more than 2.5 ml of water, formic acid and hydrogen peroxide inside the package,
    sealing the package,
    generating performic acid inside the package without the application of heat, plasmas and other activators and at substantially ambient conditions, and
    completing sterilization of the article in the package after about one hour at substantially ambient conditions.

* * * * *